(12) United States Patent
Moffitt et al.

(10) Patent No.: US 8,965,529 B2
(45) Date of Patent: Feb. 24, 2015

(54) DEVICES WITH CANNULA AND ELECTRODE LEAD FOR BRAIN STIMULATION AND METHODS OF USE AND MANUFACTURE

(71) Applicant: Boston Scientific Neuromodulation Corporation, Valencia, CA (US)

(72) Inventors: Michael Adam Moffitt, Valencia, CA (US); Paul M. Meadows, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/274,615

(22) Filed: May 9, 2014

(65) Prior Publication Data

US 2014/0249542 A1    Sep. 4, 2014

Related U.S. Application Data

(60) Continuation of application No. 14/023,022, filed on Sep. 10, 2013, now Pat. No. 8,755,906, which is a continuation of application No. 12/553,299, filed on Sep. 3, 2009, now Pat. No. 8,548,602, which is a division of application No. 11/241,156, filed on Sep. 30, 2005, now Pat. No. 8,271,094.

(51) Int. Cl.
*A61N 1/00* (2006.01)
*A61B 17/34* (2006.01)
*A61N 1/05* (2006.01)
*A61N 1/36* (2006.01)

(52) U.S. Cl.
CPC .......... *A61B 17/3468* (2013.01); *A61N 1/0529* (2013.01); *A61N 1/0534* (2013.01); *A61N 1/36017* (2013.01); *A61N 1/36025* (2013.01); *A61N 1/36082* (2013.01)
USPC ......................................................... 607/116

(58) Field of Classification Search
CPC .......................... A61B 17/3468; A61N 1/0534
USPC ......................................................... 607/116
See application file for complete search history.

(56) References Cited

U.S. PATENT DOCUMENTS

| | | | |
|---|---|---|---|
| 4,350,159 | A | 9/1982 | Gouda |
| 4,458,677 | A | 7/1984 | McCorkle, Jr. |
| 4,471,777 | A | 9/1984 | McCorkle, Jr. |
| 4,565,200 | A | 1/1986 | Cosman |
| 4,886,065 | A | 12/1989 | Collins, Jr. |

(Continued)

FOREIGN PATENT DOCUMENTS

| | | |
|---|---|---|
| EP | 1062973 A1 | 12/2000 |
| WO | 9936122 A1 | 7/1999 |

OTHER PUBLICATIONS

"System and Method for Selective Multi-Site Microelectrode Recording," IP.com, IPCOM000016587D, Jul. 1, 2003.

(Continued)

*Primary Examiner* — George Manuel
(74) *Attorney, Agent, or Firm* — Lowe Graham Jones PLLC; Bruce E. Black

(57) ABSTRACT

A device for brain stimulation includes a cannula configured and arranged for insertion into a brain of a patient; at least one cannula electrode disposed on the cannula; and an electrode lead for insertion into the cannula, the electrode lead comprising at least one stimulating electrode.

20 Claims, 5 Drawing Sheets

(56) References Cited

U.S. PATENT DOCUMENTS

| | | |
|---|---|---|
| 4,931,056 A | 6/1990 | Ghajar et al. |
| 4,955,891 A | 9/1990 | Carol |
| 5,006,122 A | 4/1991 | Wyatt et al. |
| 5,116,345 A | 5/1992 | Jewell et al. |
| 5,119,832 A | 6/1992 | Xavier |
| 5,300,080 A | 4/1994 | Clayman et al. |
| 5,318,041 A | 6/1994 | DuBois et al. |
| 5,330,485 A | 7/1994 | Clayman et al. |
| 5,462,545 A | 10/1995 | Wang et al. |
| 5,618,287 A | 4/1997 | Fogarty et al. |
| 5,752,937 A | 5/1998 | Otten et al. |
| 5,843,148 A | 12/1998 | Gijsbers et al. |
| 5,925,073 A | 7/1999 | Chastain et al. |
| 6,011,996 A | 1/2000 | Gielen et al. |
| 6,026,567 A | 2/2000 | Swoyer et al. |
| 6,066,165 A | 5/2000 | Racz |
| 6,181,971 B1 | 1/2001 | Doan |
| 6,261,300 B1 | 7/2001 | Carol et al. |
| 6,301,492 B1 | 10/2001 | Zonenshayn |
| 6,343,226 B1 | 1/2002 | Sunde et al. |
| 6,356,792 B1 | 3/2002 | Errico et al. |
| 6,413,263 B1 | 7/2002 | Lobdill et al. |
| 6,416,520 B1 | 7/2002 | Kynast et al. |
| 6,456,869 B1 | 9/2002 | Raylman et al. |
| 6,456,889 B2 | 9/2002 | Pianca et al. |
| 6,456,890 B2 | 9/2002 | Pianca et al. |
| 6,564,078 B1 | 5/2003 | Marino et al. |
| 6,572,624 B2 | 6/2003 | U et al. |
| 6,597,953 B2 | 7/2003 | Boling |
| 6,606,521 B2 | 8/2003 | Paspa et al. |
| 6,694,162 B2 | 2/2004 | Hartlep |
| 6,829,508 B2 | 12/2004 | Schulman et al. |
| 7,004,948 B1 | 2/2006 | Pianca et al. |
| 7,033,326 B1 | 4/2006 | Pianca et al. |
| 7,092,765 B2 | 8/2006 | Geske et al. |
| 7,177,701 B1 | 2/2007 | Pianca |
| 7,271,094 B2 | 9/2007 | Conrad |
| 7,313,442 B2 | 12/2007 | Velasco et al. |
| 7,369,899 B2 | 5/2008 | Malinowski et al. |
| 7,437,193 B2 | 10/2008 | Parramon et al. |
| 7,809,446 B2 | 10/2010 | Meadows |
| 8,271,094 B1 | 9/2012 | Moffitt et al. |
| 8,548,602 B2 | 10/2013 | Moffitt et al. |
| 2001/0027336 A1 | 10/2001 | Gielen et al. |
| 2003/0120328 A1 | 6/2003 | Jenkins et al. |
| 2004/0059348 A1 | 3/2004 | Geske et al. |
| 2004/0059392 A1 | 3/2004 | Parramon et al. |
| 2004/0098074 A1* | 5/2004 | Erickson et al. ............. 607/117 |
| 2004/0116977 A1 | 6/2004 | Finch et al. |
| 2006/0025841 A1* | 2/2006 | McIntyre .................... 607/116 |

OTHER PUBLICATIONS

"Universal Instrument Guide and Surgical Insertion Tool for Stereotactic Frames," IP.com, IPCOM000011023D, Feb. 7, 2003.

Karmarkar et al., "Active Microelectrode Systems for MRI-guided Inracranial Interventions: A Feasibility Study," Universitat Leipzig, http://www.uni-leipzig.de/radiologie/start/archive/5thinterventional/Abstracts%20POSTERS/P11%20Active%20Microelectrode%20Systems%20for%20for%20MRI-guided%20Intracranial%10Interventions.pdf.

Official Communication for U.S. Appl. No. 11/241,156 mailed Oct. 16, 2008.

Official Communication for U.S. Appl. No. 11/241,156 mailed Apr. 30, 2009.

Official Communication for U.S. Appl. No. 11/241,156 mailed Dec. 9, 2009.

Official Communication for U.S. Appl. No. 12/553,299 mailed Jul. 1, 2011.

Official Communications for U.S. Appl. No. 12/553,299 mailed Oct. 26, 2011.

Official Communications for U.S. Appl. No. 12/553,229 mailed Mar. 19, 2012.

Official Communication for U.S. Appl. No. 12/553,299 mailed Jun. 12, 2012.

Official Communication for U.S. Appl. No. 11/241,156 mailed Jan. 8, 2008.

Official Communication for U.S. Appl. No. 11/241,156 mailed Jun. 6, 2008.

Official Communication for U.S. Appl. No. 12/553,299 mailed Nov. 21, 2012.

Official Communications for U.S. Appl. No. 14/023,022 mailed Nov. 6, 2013.

* cited by examiner

US 8,965,529 B2

DEVICES WITH CANNULA AND ELECTRODE LEAD FOR BRAIN STIMULATION AND METHODS OF USE AND MANUFACTURE

RELATED APPLICATIONS

This application is a continuation of U.S. patent application Ser. No. 14/023,022 filed Sep. 10, 2013, now allowed, which is a continuation of U.S. patent application Ser. No. 12/553,299 filed Sep. 3, 2009, which issued as U.S. Pat. No. 8,548,602, which is a divisional of U.S. patent application Ser. No. 11/241,156 filed Sep. 30, 2005, which issued as U.S. Pat. No. 8,271,094, all of which are incorporated herein by reference.

FIELD

The invention is directed to devices and methods for brain stimulation including deep brain stimulation. In addition, the invention is directed to devices and methods for brain stimulation using a cannula with at least one cannula electrode and an electrode lead with at least one stimulating electrode.

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons. To more precisely determine the target location, a recording lead with a recording electrode at or near the tip of the recording lead can be inserted into the brain of the patient, and physiological maps can be generated. Typically, the recording lead is guided to the target location within the brain using a stereotactic frame and microdrive motor system.

As the recording lead is moved through the brain, field voltages and single unit voltages axe observed with the recording electrode. Observation with the electrode (i.e., physiological mapping) may include activating the target neurons to generate electrical signals that can be received by the recording electrode. The mapping approach may also include electrical stimulation via the electrode that is also used for recording. Once the position of the target neurons is determined, the recording lead can be removed and the stimulating lead inserted. The object of using the recording lead followed by insertion of the stimulating lead is to position the stimulating lead as near as possible to the target neurons. The precise insertion of the stimulating lead and positioning of the stimulating lead in the precise location indicated by the recording lead can be particularly difficult. In some instances, multiple insertions of the recording lead are used for mapping, and multiple insertions of a stimulating lead may need to occur to properly position the stimulating electrode.

BRIEF SUMMARY

One embodiment is a device for brain stimulation that includes a cannula configured and arranged for insertion into a brain of a patient; at least one cannula electrode disposed on the cannula; and an electrode lead for insertion into the cannula. The electrode lead includes at least one stimulating electrode.

Another embodiment is a method of stimulating a portion of a brain of a patient. A cannula is inserted into the brain of the patient. The cannula includes at least one cannula electrode. Tissue to be stimulated is identified using the cannula electrode(s). An electrode lead is inserted into the cannula prior to, during, or after insertion of the cannula into the brain of the patient. The electrode lead includes at least one stimulating electrode. The cannula is removed from the brain leaving the electrode lead in place. The tissue is stimulated using die stimulating electrode(s).

Yet another embodiment is a cannula for insertion of an electrode lead to stimulate brain tissue. The cannula includes a cannula body configured and arranged to receive the electrode lead and a plurality of cannula electrodes disposed on the cannula body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of devices and methods for brain stimulation including deep brain stimulation. In addition, the invention is directed to devices and method tor brain stimulation using a cannula with ax least one cannula electrode and an electrode lead with at least one stimulating electrode.

Existing techniques of brain stimulation often use multiple penetrations into the brain to locate the tissue to be stimulated and to position the stimulating electrode. Each penetration is associated with a possibility of hemorrhage. In addition, using one lead for identifying the desired tissue for stimulation and a second lead for stimulating the tissue can result in errors associated with the placement of the second lead. Sources of error can include, for example, errors associated with the stereotactic apparatus; slipping into a previous penetration tract when several tracts have been made in the effort to find the tissue to be stimulated; and displacement of tissue with each penetration. Because of these concerns, some clinical centers do not use recording electrodes to identify the tissue to be stimulated and, therefore, have a lower probability of accurately placing the electrode lead with the stimulating electrode. Further, each penetration with a microelectrode under current paradigms can increase the cost of surgery by extending the operating room time and including additional time from a neurologist to aid in physiological mapping.

A device for deep brain stimulation can include a cannula with one or more cannula electrodes and an electrode lead, which is inserted into the cannula, that contains one or more stimulating electrodes. The cannula electrodes in the cannula can be used to identify the tissue to be stimulated and then the cannula can be removed leaving the electrode lead with the stimulating electrode(s) in place. This allows a practitioner to determine the position of the target neurons using the cannula electrode(s) and position the stimulating electrode(s) accordingly without removal of a recording lead and insertion of a separate stimulation lead. The cannula can include cannula electrodes spaced around the circumference of the lead to more precisely determine the position of the target neurons. The cannula electrodes can be used as recording electrodes, stimulating electrodes, or both, if desired. In addition, it will be recognized that stimulating electrodes may be used as recording electrodes and recording electrodes may be used as stimulating electrodes.

Figure 1:
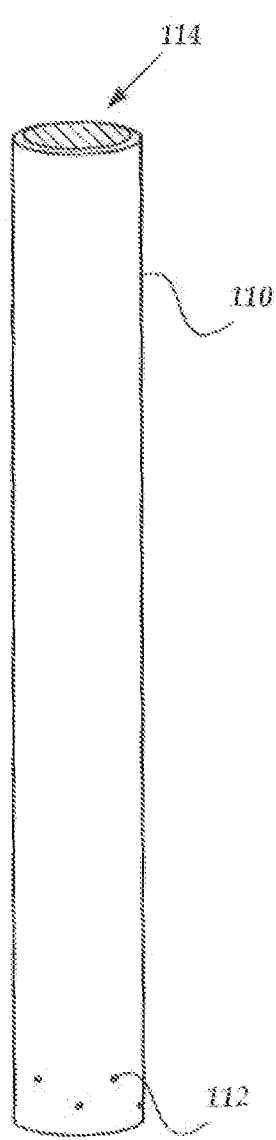
FIG. 1 is a schematic perspective side view of one embodiment of a cannula, according to the invention.
Figure 2:
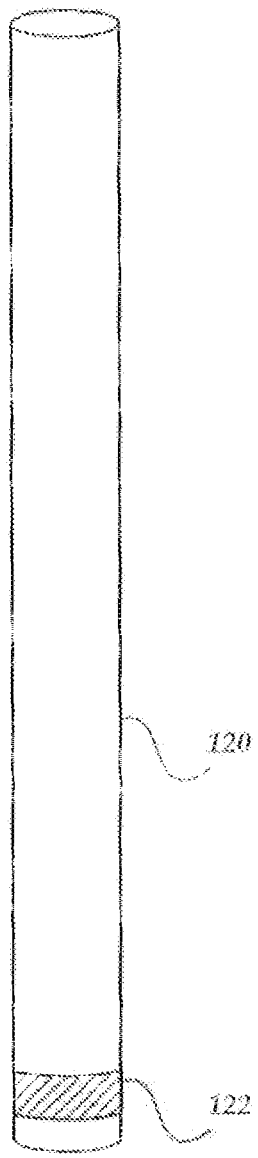
FIG. 2 is a schematic side view of one embodiment of an electrode lead, according to the invention.
Figure 3:
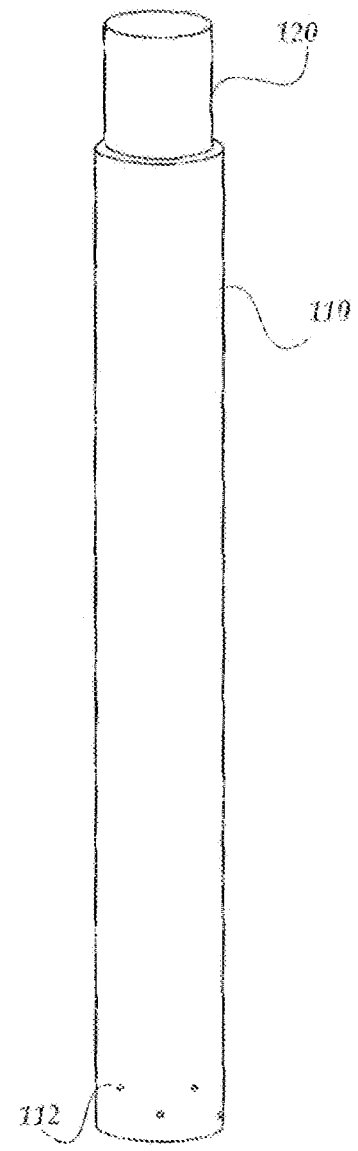
FIG. 3 is a schematic side view of the electrode lead of FIG. 2 inserted in the cannula of FIG. 1.
Figure 7:
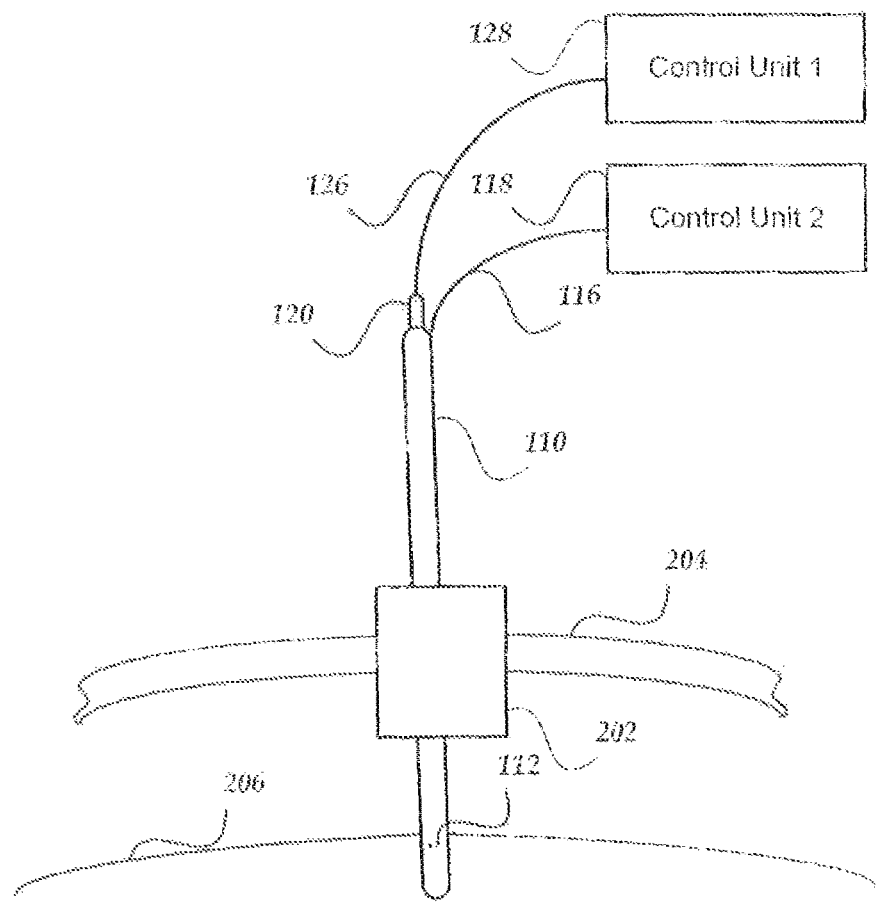
FIG. 7 is a schematic side view of a lead and associated hardware for insertion into a cranium, according to the invention.

FIG. 1 illustrates one embodiment of a cannula 110 FIG. 2 illustrates one embodiment of an electrode lead 120, and FIG. 3 illustrates the cannula and electrode lead together. The cannula 110 includes one or more cannula electrodes 112 and defines a lumen 114 through which the electrode lead 120 can be inserted. As illustrated in FIG. 7, the cannula 110 also includes conductors 116 disposed within the cannula or in the lumen that extend from each of the cannula electrodes 112 out of the cannula to a control unit 118.

The cannula 110 can be formed of any non-conducting material such as, for example, a plastic material. Preferably, the cannula 110 is formed of a substantially rigid material (e.g., sufficiently rigid for insertion in the brain without buckling) winch facilitates insertion of the cannula into the brain of the patient and positioning of the cannula and electrode lead near the tissue to be stimulated. In some embodiments, the cannula 110 is a disposable unit so that it is discarded alter use and does not need to be subsequently sterilized for reuse.

The cannula electrode(s) 112 can be made using a metal, alloy, conductive oxide, or other conductive material. Examples of suitable materials include platinum, iridium, platinum iridium alloy, stainless steel, titanium, and tungsten.

Any type of electrode can be used for the cannula electrodes including monopolar recording electrodes, bipolar recording electrodes (see FIG. 4), other multipolar recording electrodes, and any type of stimulating electrode arrangement. In at least some embodiments, bipolar or other multipolar recording electrodes are preferred because they can assist in finding nearby electrical signals, while disregarding or reducing distant electrical signals by observation of the differential between the signals from, the two or more, closely-spaced electrodes. It will be recognized that the cannula electrodes can all be the same or that different types of cannula electrodes can be used on a single cannula.

Any cannula electrode configuration can be used including electrode pads or plates. A preferred cannula electrode for at least some embodiments is a tip of a wire. This type of electrode can assist in more precise location of the target neurons because of the small surface area for detection of electrical signals. Such cannula electrodes may have a diameter of no more than 200 μm or no less than 1 μm. The diameter may be in the range from, for example, 25 μm to 100 μm. In one embodiment, the cannula electrodes 112 correspond to wire conductors that extend out of the cannula 110 and are then trimmed or ground down flush with the cannula surface.

Figure 4:
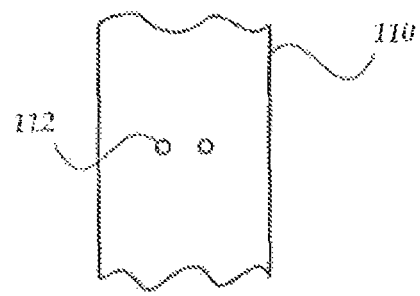
FIG. 4 is a schematic side view of one embodiment of a recording electrode arrangement, according to the invention.

In at least some embodiments, cannula electrodes 112 are arranged at various positions around the lateral circumference of the cannula 110. In these arrangements, the cannula electrodes are positioned in irregular or, preferably, regular intervals around the cannula. For example, in FIG. 1, the cannula electrodes 112 are positioned in rings around the cannula with about 90° separation between neighboring cannula electrodes of a particular ring. In other embodiments, the cannula electrodes 106 are positioned around the lead with about 60°, 72°, 120°, 180°, or any other angular separation between neighboring cannula electrodes. In addition, cannula electrodes can be formed in one or more rings around the circumference of the cannula 110. FIG. 1 illustrates one embodiment with two rings. FIG. 4 illustrates an embodiment with pairs of recording electrodes 112 (e.g., bipolar recording electrodes) forming a single ring around the circumference of the cannula. Positioning the cannula electrodes 112 around the cannula 110 in this manner can assist in determining the position of the target neurons because the cannula electrodes, individually or in pairs (or any other grouping), can sample the brain tissue around the cannula without rotating the cannula. In another embodiment, electrodes can be disposed in a helical arrangement around the cannula. The cannula can then be rotated to sample the tissue using the electrodes.

The cannula is hollow with a central region 114 that receives the electrode lead 120. Preferably, the electrode lead 120 slides into the cannula relatively easily and the cannula can also be slid off the electrode lead once the correct tissue has been located. Generally, when the electrode lead is inserted in the cannula, the stimulating electrodes of the electrode lead are aligned with lire cannula electrodes of the cannula, as illustrated in FIG. 3. Angular alignment of stimulating electrodes with cannula electrodes may also be practiced if the stimulating electrodes are not ring-shaped. Preferably, the relative alignments of the contacts on the cannula and on the electrode lead are always known, for example, by holding the electrode lead firmly so that the relative alignments are not accidentally altered. In some embodiments, markings or other indicia are provided on the electrode lead and/or cannula to facilitate alignment of the electrode lead with the cannula. The electrode lead 120 typically includes one or more stimulating electrodes 122 disposed on the lead for stimulating the target tissue. In at least some embodiments, the electrode lead 120 is substantially less rigid than the cannula 110 to reduce or avoid damage to the brain tissue with extended implantation and use of the lead. The electrode lead 120 cars be formed of a non-conducting material such as, for example, a polymeric material. Suitable polymeric materials include, for example, silicone rubber and polyethylene. Preferably, the lead is made using a biocompatible material. In at least some instances, the lead may be in contact with body tissue for extended periods of time.

In at least some embodiments, the electrode lead 120 has a cross-sectional diameter of, for example, no more than 1.5 mm and the diameter may be in the range of 1 to 1.2 mm. The lead may have a length of, for example, at least 10 mm and the length of the lead may be in the range of 10 to 120 mm.

The electrode lead 120 includes one or more stimulating electrodes 122 arranged along the longitudinal axis of the lead, preferably, near a distal end of the lead. In at least some embodiments, the lead includes a plurality of stimulating electrodes. A conductor is attached to each stimulating electrode 122 and exits the electrode lead for connection to a control unit 128. In at least some embodiments, the stimulating electrodes have a surface area of at least 1 mm$^2$ or at least 5 mm$^2$. The surface area may be in the range from, for example, 1 mm$^2$ to 12 mm$^2$.

Figure 5:
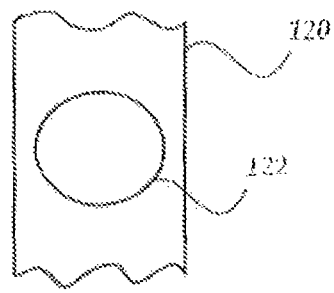
FIG. 5 is a schematic side view of one embodiment of a stimulating electrode arrangement, according to the invention.
Figure 6:
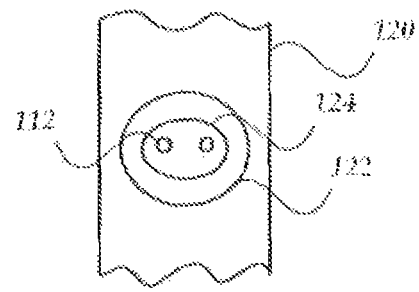
FIG. 6 is a schematic side view of one embodiment of a recording electrode and stimulating electrode arrangement, according to the invention.

In some embodiments, a stimulating electrode 122 forms a ring that fully or substantially encircles the lead 120, as illustrated in FIGS. 2 and 3. In other embodiments, the stimulating electrodes are not rings, but are instead discrete shapes disposed on one side (or multiple sides) of the lead, as illustrated, for example, in FIGS. 5 and 6. A variety of shapes can be used tor the stimulating electrodes including, for example, rings, circles, ovals, squares, rectangles, triangles, etc. Stimulating electrodes 112 can be positioned around the circumference of the lead 120 in a similar manner to that described for the cannula electrodes.

The electrode lead 120 may also include one or more recording electrodes disposed on the lead. Optionally, one or more of the recording electrodes can be positioned within one or more of the stimulating electrode using an arrangement such as that illustrated in FIG. 6. In this arrangement, there is a nonconducting region 124 separating the stimulating electrode 122 and the recording electrode 112. Other suitable electrode arrangements are described in U.S. Pat. No. 7,809, 446, incorporated herein by reference.

The stimulating electrodes can be made using a metal, alloy, conductive oxide or other conductive material. Examples of suitable materials include platinum, iridium, platinum iridium alloy, stainless steel, titanium, or tungsten. Preferably, the stimulating electrodes are made of a material that is biocompatible and does not substantially corrode under expected operating conditions in the operating environment for the expected duration of use.

Conductors that attach to the stimulating electrode(s) 122 also pass through the electrode lead 120. The conductors 126 continue to connect to a control unit 128 (see FIG. 7). The control unit 128 provides stimulation signals, often in the form of pulses, to the stimulating electrodes 122. This control unit 128 can be the same as the control unit 118 coupled to the cannula electrodes.

In one example of implantation of the electrode lead illustrated in FIG. 7, access to the desired position in the brain can be accomplished by drilling a hole in the patient's skull or cranium 206 with a cranial drill (commonly referred to as a burr), and coagulating and incising the dura mater, or brain covering. The electrode lead 120 can be inserted into the cranium and brain tissue with the assistance of the cannula 110. The electrode lead can be placed in the cannula prior to, simultaneously with, or after insertion of the cannula into the brain of the patient. The cannula and electrode lead can be guided to the target location within the brain using, for example, a stereotactic frame 204 and a microdrive motor system 202, or a frameless microdrive system.

The cannula electrode(s) 112 on the cannula 110 can be observed using a control unit 118 attached to the conductors 116 extending from, the cannula 110 to identify the target neurons. Once the target tissue is identified, the cannula can be removed leaving the electrode lead and associated stimulating electrode(s). The stimulating electrodes can then be activated to provide the desired stimulation to the target neurons by coupling the stimulating electrode 122 to a control unit 128 via conductors 126. The cannula electrodes can also be used to provide stimulation. In some instances, the stimulation provided by the cannula electrodes is temporary and is unavailable when the cannula is removed. The control unit 128 can be the same or different from the control unit 118 used with the cannula electrodes 112. The control unit 128 can also be used to operate any recording electrodes on the lead.

In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulating electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Figure 8:
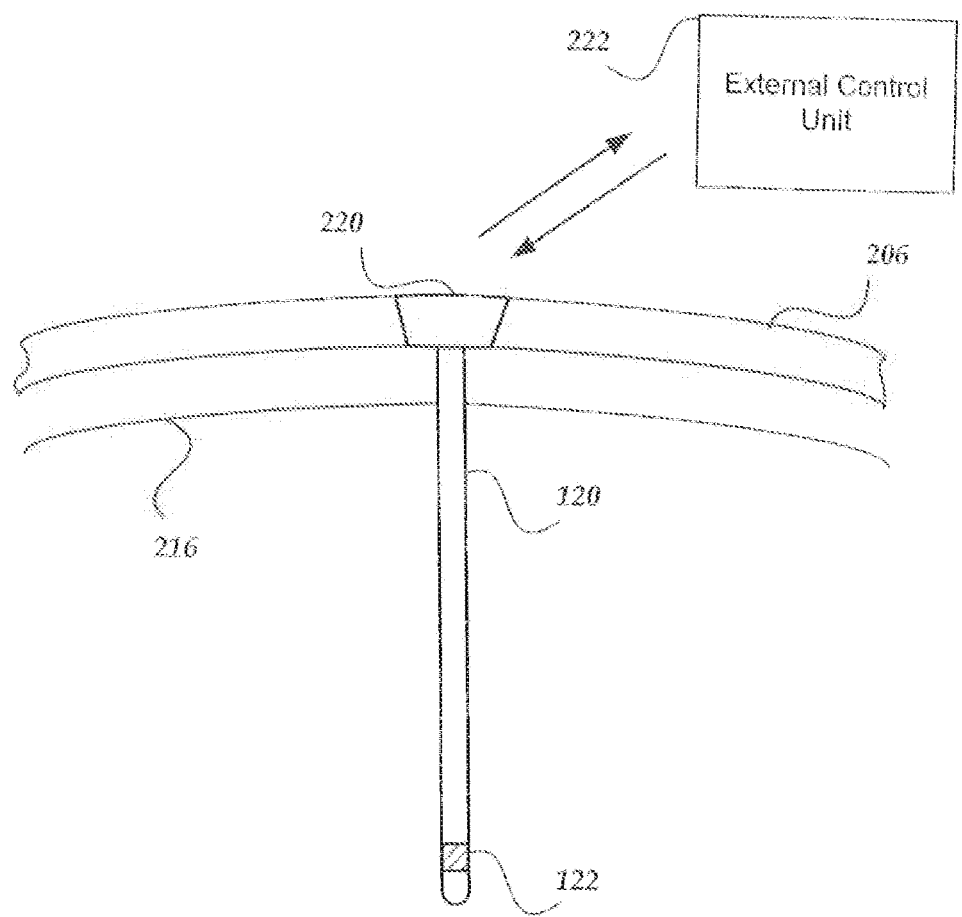
FIG. 8 is a schematic side view of one embodiment of a lead with an implantable pulse generator unit, according to the invention.

FIG. 8 illustrates another embodiment that includes a lead 120 and an implantable pulse generator unit 220 coupled to the lead. The lead 120 includes one or mote stimulating electrodes 122 and, optionally, one or more recording electrodes. The arrangement of these electrodes can be selected as described above. The stimulating electrode(s) 122 and, optionally, any recording electrodes, are coupled to the implantable pulse generator unit 220 by conductors running through the lead 120.

The implantable pulse generator unit 220 can be permanently or detachable coupled to the lead 120. In some embodiments, the lead 120 has a connector (not shown) that can be coupled to the implantable pulse generator unit 220 before, during, or alter implantation of the lead into the brain tissue 216. In one embodiment, the lead 120 is implanted as illustrated and discussed relative to FIG. 7. The implantable pulse generator is then coupled to the lead after implantation. In another embodiment, the implantable pulse generator is coupled to the lead during implantation and the implantable pulse generator provides signals from the recording electrodes to an external control unit to determine the tissue to be stimulated. Once the lead is implanted and positioned, the implantable pulse generator is implanted.

The implantable pulse generator can be implanted in any convenient portion of the body including in the neck or behind the ear. In one embodiment, the implantable pulse generator is implanted in the burr hole in the patient's skull 206 formed for insertion of the lead 120. Preferably, the implantable pulse generator does not extend substantially outside the exterior of the skull. Preferably, the implantable pulse generator is adhesively attached to the skull and/or a plate is positioned over the burr hole and attached to the skull or scalp to keep the implantable pulse generator in place. Preferably, the implantable pulse generator does not extend too far into the cranial cavity so that contact with brain tissue is avoided.

Figure 9:
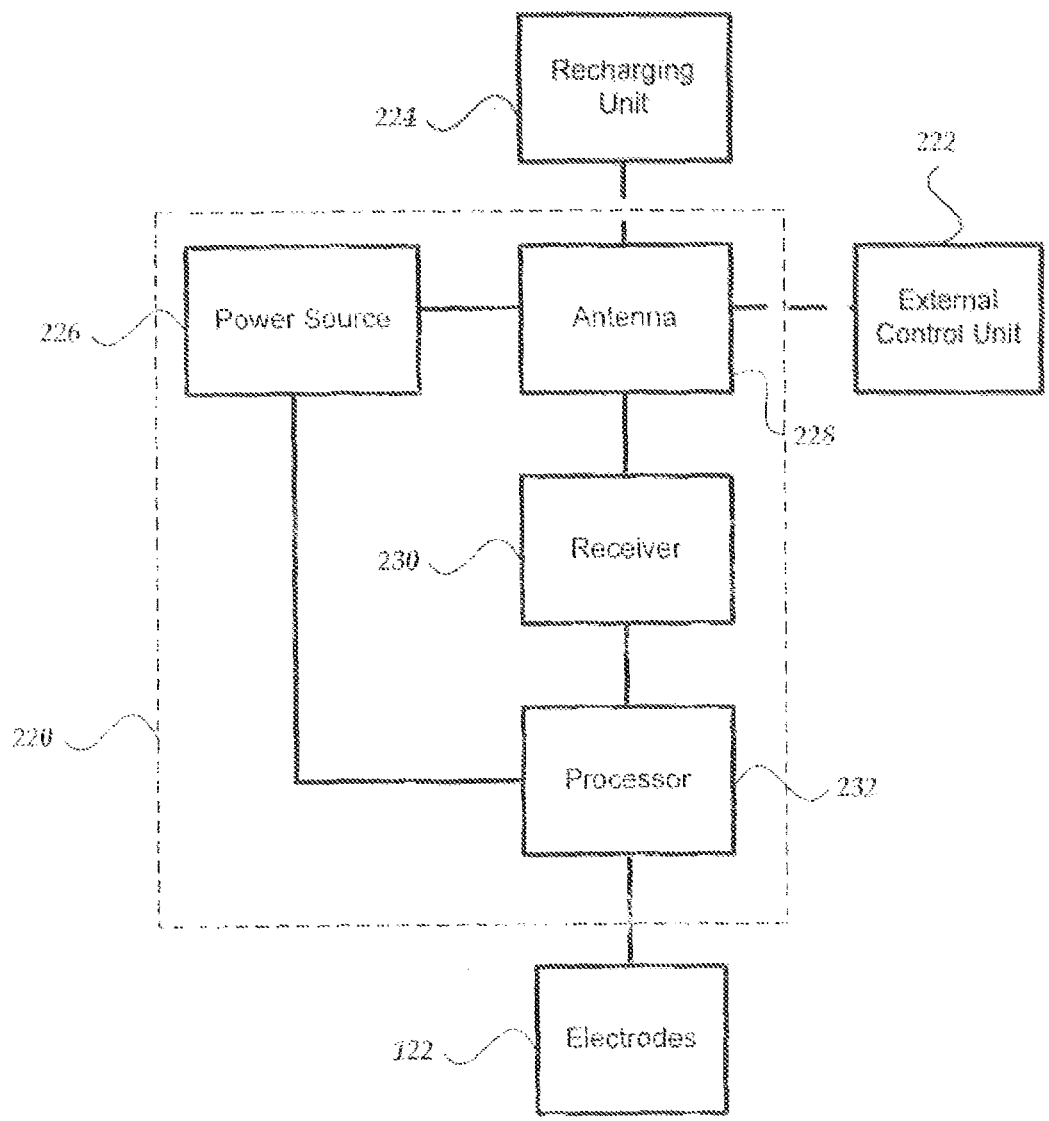
FIG. 9 is a schematic block diagram of one embodiment of an implantable pulse generator unit, according to the invention.

The implantable pulse generator unit 220 provides pulses of electrical energy to the stimulating electrode(s) 122 to stimulate the desired brain tissue. In some embodiments, the implantable pulse generator unit can also perform one or more other functions such as, for example, receiving signals from the recording electrodes; evaluating signals from the recording electrodes; altering or adjusting stimulation pulse parameters such as, for example, pulse frequency, pulse duration, pulse waveform, and pulse strength, as well as determining which electrodes sink and source the current comprising the pulse; transmitting information to an external control unit 222; receiving signals, such as control signals or information, from an external control unit 222. The implantable pulse generator can include a power source 226, as illustrated in FIG. 9. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via an optional antenna 228. The external power source can be in a device that is mounted on the skin of the user or in a unit that, is provided near the patient on a permanent or periodic basis.

If the power source 226 is a rechargeable battery, the battery may be recharged using the optional antenna 228, if desired. Power can be provided to the battery 226 for recharging by inductively coupling the battery through the antenna to a recharging unit 224 external to the patient.

A processor 232 is typically provided in the implantable pulse generator to control the timing and electrical characteristics of the pulses sent to the electrodes. For example, the processor can, if desired, control one or more of the timing, periodicity, strength, duration, and waveform of the pulses. Any processor can be used and can be as simple as an electronic device that produces pulses at a regular interval or the processor can be capable of receiving and interpreting instructions from an external control unit 222.

In one embodiment, the antenna 228 is capable of receiving signals (e.g., RF signals) front an external control unit 222. The external control unit 222 can be device that is worn on the skin of the user or can be carried by the user and can have a form similar to a pager or cellular phone, if desired. As another alternative, the external control unit 222 may not be worn or carried by the user but may only be available at, for example, a home station or at a clinician's office.

The signals sent to the processor 232 via the antenna 228 and receiver 230 can be used to modify or otherwise direct the operation of the implantable pulse generator. For example, the signals may be used to modify the pulses of the implantable pulse generator such as modifying one or more of pulse duration, pulse frequency, pulse waveform, and pulse strength. The signals may also direct the implantable pulse generator to cease operation or to start operation or to start charging the battery. Additionally or alternatively, the implantable pulse generator can include a port into which a lead to the external control unit can be plugged so that information, control signals, or the like can be transmitted or received through a wired connection.

Optionally, the implantable pulse generator may include a transmitter (not shown) coupled to the processor and antenna tor transmitting signals back to the external control unit 222 or another unit capable of receiving die signals. For example, the implantable pulse generator may transmit signals indicating whether the implantable pulse generator is operating properly or not or indicating when the battery needs to be charged. The processor may also be capable of transmitting information about the pulse characteristics so that a user or clinician can determine or verity the characteristics. In some embodiments, the implantable pulse generator can send back signals to the external control unit from any recording electrodes on the lead 120. Such signals may be used to monitor the stimulation treatment, to verify that the lead is still correctly positioned, or to assist in the implantation procedure.

The implantable pulse generator may include information storage capacity. Ibis can be used to store pulse parameters and the like, as well as information that can be later transmitted to the external control unit 222.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A system for brain stimulations comprising
   an electrode lead configured and arranged for insertion into a brain of a patient, the electrode lead comprising a plurality of stimulating electrodes, wherein at least a portion of the stimulating electrodes are disposed on multiple sides of the electrode lead and individually have a non-ring shape; and
   a cannula configured and arranged to receive the electrode lead and to aid in insertion of a portion of the electrode lead into the brain through the cannula followed by removal of the cannula leaving the portion of the electrode lead in the brain, the cannula comprising a cannula body configured and arranged for insertion into the brain and to receive the electrode lead, and a plurality of cannula electrodes disposed on the cannula body.

2. The system of claim 1, wherein the portion of the stimulation electrodes are disposed in a plurality of rings around a circumference of the electrode lead.

3. The system of claim 2, wherein the stimulation electrodes in each of the plurality of rings are disposed in regular intervals around the circumference of the electrode lead.

4. The system of claim 2, wherein the rings are spaced apart from each other at different lateral distances from a tip of the electrode lead.

5. The system of claim 2, wherein the stimulation electrodes in each of the plurality of rings are at 120° intervals around the circumference of the electrode lead.

6. The system of claim 2, wherein at least a portion of the cannula electrodes are disposed in a plurality of rings around a circumference of the cannula body.

7. The system of claim 6, wherein the rings of cannula electrodes are longitudinally separated from each other and each of the plurality of rings of cannula electrodes comprises at least two of the plurality of cannula electrodes.

8. The system of claim 1, wherein the non-ring shape is a square or a rectangle.

9. The system of claim 1, wherein the non-ring shape is a circle or an oval.

10. The system of claim 1, further comprising markings on the cannula and electrode lead to facilitate alignment of the electrode lead with the cannula.

11. The system of claim 1, wherein the electrode lead is substantially less rigid than the cannula.

12. A method of stimulating a portion of a brain of a patient, the method comprising:
    providing the system of claim 1;
    inserting the cannula into the brain of the patient;
    using at least one of the plurality of cannula electrodes to find tissue to be stimulated, repositioning the cannula as needed to find the tissue to be stimulated;
    inserting the electrode lead into the cannula;
    removing the cannula from the brain leaving the electrode lead in place; and
    stimulating the tissue using at least one of the stimulating electrodes.

13. The method of claim 12, wherein inserting the electrode lead into the cannula comprises aligning a one of the stimulating electrodes with a one of the cannula electrodes of the cannula that is adjacent the tissue found for stimulation.

14. A system for brain stimulation, comprising
an electrode lead configured and arranged for insertion into a brain of a patient, the electrode lead comprising a plurality of stimulating electrodes, wherein at least a portion of the stimulating electrodes are disposed in a helical arrangement around the electrode lead and individually have a non-ring shape; and
a cannula configured and arranged to receive the electrode lead and to aid in insertion of a portion of the electrode lead into the brain through the cannula followed by removal of the cannula leaving the portion of the electrode lead in die brain, the cannula comprising a cannula body configured and arranged for insertion into the brain and to receive the electrode lead, and a plurality of cannula electrodes disposed on the cannula body.

15. The system of claim 14, wherein the non-ring shape is a square or a rectangle.

16. The system of claim 14, further comprising markings on the cannula and electrode lead to facilitate alignment of the electrode lead with the cannula.

17. The system of claim 14, wherein the electrode lead is substantially less rigid than the cannula.

18. The system of claim 14, wherein at least a portion of the cannula electrodes are disposed in a helical arrangement around the cannula body.

19. A method of stimulating a portion of a brain of a patient, the method comprising:
providing the system of claim 14;
inserting the cannula into the brain of the patient;
using at least one of the plurality of cannula electrodes to find tissue to be stimulated, repositioning the cannula as needed to find the tissue to be stimulated;
inserting the electrode lead into the cannula;
removing the cannula from the brain leaving the electrode lead in place; and
stimulating the tissue using at least one of the stimulating electrodes.

20. The method of claim 19, wherein inserting the electrode lead into the cannula comprises aligning a one of the stimulating electrodes with a one of the cannula electrodes of the cannula that is adjacent the tissue found for stimulation.

* * * * *